US012799130B2

(12) United States Patent
Roscoe et al.

(10) Patent No.: US 12,799,130 B2
(45) Date of Patent: Nov. 17, 2026

(54) SPIRO-COMPOUNDS AND COMPOSITIONS INCLUDING THE SAME

(71) Applicant: Solventum Intellectual Properties Company, Maplewood, MN (US)

(72) Inventors: Stephen B. Roscoe, Woodbury, MN (US); Paul J. Homnick, Lake Elmo, MN (US); Ahmed S. Abuelyaman, Woodbury, MN (US)

(73) Assignee: Solventum Intellectual Properties Company, Eagan, MN (US)

( * ) Notice: Subject to any disclaimer, the term of this patent is extended or adjusted under 35 U.S.C. 154(b) by 338 days.

(21) Appl. No.: 18/555,213

(22) PCT Filed: Apr. 4, 2022

(86) PCT No.: PCT/IB2022/053129

§ 371 (c)(1),
(2) Date: Oct. 12, 2023

(87) PCT Pub. No.: WO2022/248947

PCT Pub. Date: Dec. 1, 2022

(65) Prior Publication Data

US 2024/0208990 A1 Jun. 27, 2024

Related U.S. Application Data

(60) Provisional application No. 63/193,447, filed on May 26, 2021.

(51) Int. Cl.
*C07D 493/10* (2006.01)

(52) U.S. Cl.
CPC .................................. *C07D 493/10* (2013.01)

(58) Field of Classification Search
CPC .................................................... C07D 493/10
USPC .......................................................... 549/334
See application file for complete search history.

(56) References Cited

U.S. PATENT DOCUMENTS 3,477,990 A 11/1969 Dante et al.

FOREIGN PATENT DOCUMENTS

WO 2016014536 1/2016
WO 2020115661 A1 6/2020
WO 2022112886 A1 6/2022

OTHER PUBLICATIONS

Dixit, "Condensation of phenols and phenolic ethers with acetone dicarboxylic acid. Use of condensing agents other than sulphuric acid. A new non-acidic condensation product", Journal of the Indian Chemical Society, Jul. 1945, vol. 22, No. 7, pp. 207-213.

Dixit, "Sulphuryl Chloride: A new condensing agent for the pechmann-reaction. Isolation of trans B-2: 4-dihydroxy-phenyl-glutaconic acid", Proceedings—Indian Academy of Sciences, Section A, 1948, vol. 27A, pp. 14-22.

Dubovik, "4,4'-Spirodichroman-2-onesasunexpected products from the condensation of resorcinols and dimethyl acetonedicarboxylate", Chemistry of Heterocyclic Compounds, 2007, vol. 43, No. 3, pp. 277-281, XP019499559.

International Search Report for PCT International Application No. PCT/IB2022/053129, mailed on Jun. 23, 2022, 4 pages.

Păunescu, "A versatile access to new halogenated 7-azidocoumarins for photoaffinity labeling: Synthesis and photophysical properties", Dyes and Pigments, May 2011, vol. 91, pp. 427-434, XP028243243.

*Primary Examiner* — Kahsay Habte

(57) ABSTRACT

A spiro-compound represented by the formula presented below. Each Z independently represents $CH_2$ or a direct bond, wherein at least one Z represents a direct bond. Each $R^1$ independently represents H, $C_1$-$C_6$ alkyl, hydroxyl, or a halogen. Each $R^2$ independently represents H or a monovalent organic group having from 1 to 36 carbon atoms. Each $R^3$ independently represents H, $C_1$-$C_6$ alkyl, or halogen. Curable compositions including some of the same are also disclosed.

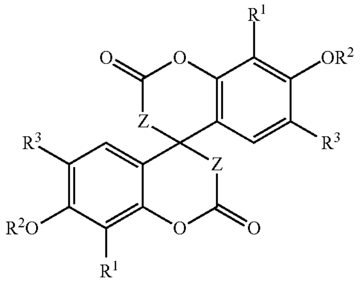

12 Claims, No Drawings

SPIRO-COMPOUNDS AND COMPOSITIONS INCLUDING THE SAME

CROSS REFERENCE TO RELATED APPLICATIONS

This application is a national stage filing under 35 U.S.C. § 371 of PCT/IB2022/053129, filed Apr. 4, 2022, which claims the benefit of Provisional Application No. 63/193,447, filed May 26, 2021, the disclosures of which are incorporated by reference in their entirety herein.

SUMMARY

The present disclosure provides compounds having a spiro-fused aromatic central core. The compounds are relatively easy and inexpensive to make, and are useful intermediates for use in chemical syntheses. For example, in many embodiments, they are, or can readily be converted into, mono- or di-functional monomers that may exhibit after polymerization at least one of reduced shrinkage and/or improved adhesive properties.

In one aspect, the present disclosure provides a spiro-compound represented by the formula

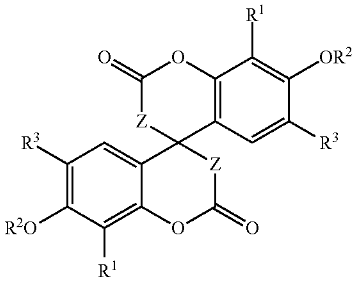

wherein:

- each Z independently represents $CH_2$ or a direct bond, wherein at least one Z represents a direct bond;
- each $R^1$ independently represents H, $C_1$-$C_6$ alkyl, hydroxyl, or a halogen;
- each $R^2$ independently represents H or a monovalent organic group having from 1 to 36 carbon atoms; and
- each $R^3$ independently represents H, $C_1$-$C_6$ alkyl, or halogen.

In another aspect, the present disclosure provides curable compositions comprising a polymerizable spiro-compound (e.g., a free-radically polymerizable monomer) according to the present disclosure and a curative for the polymerizable spiro-compound.

As used herein:

- the term "direct bond" as applied to a divalent group Z in a structural element such as A-Z-B means that A is directly bonded to B as though Z is not present (i.e., A-B);
- the term "halogen" refers to fluorine, chlorine, bromine, or iodine;
- the term "hydrocarbyl" refers to a monovalent group composed of carbon and hydrogen; and
- the terms (meth)acryloyl and (meth)acryl are equivalent, and refer to acryl and/or methacryl.

The term "heterohydrocarbyl" refers to a hydrocarbyl group in which at least one carbon atom is replaced (adjusted for valence) by O, NR, and/or S, wherein R represents H or an alkyl group (e.g., methyl or ethyl). Accordingly. ether, ester (including lactone), amide (including lactam), thioether, amine, and alkylamine are among various possible functionalities encompassed by the term "heterohydrocarbyl".

Features and advantages of the present disclosure will be further understood upon consideration of the detailed description as well as the appended claims.

DETAILED DESCRIPTION

Spiro-compounds according to the present disclosure are useful, for example, as chemical intermediates in the manufacture of polymerizable monomers such as epoxides, and can also be used as raw materials in the synthesis of polymers such as polycarbonates, poly(meth)acrylates, and/or polyesters, and provide synthetic routes to the potential development of new pharmaceuticals.

Spiro-compounds according to the present disclosure are represented by the formula

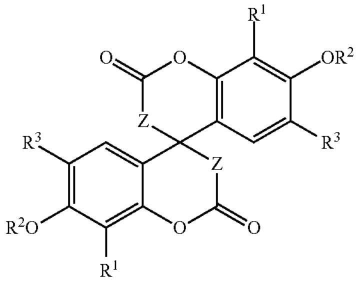

Each Z independently represents $CH_2$ or a direct bond, and at least one Z represents a direct bond. In many embodiments, both Z independently represent a direct bond.

Each $R^1$ and $R^3$ independently represents H, $C_1$-$C_6$ alkyl, hydroxyl, or halogen. In some embodiments, each $R^1$ independently represents $C_1$-$C_4$ alkyl or $C_1$-$C_3$ alkyl. Exemplary $R^1$ and $R^3$ alkyl groups include methyl, ethyl, propyl, isopropyl, butyl, isobutyl, tert-butyl, isopentyl, pentyl, hexyl, and isohexyl. Of these, methyl and ethyl are often preferred. To facilitate synthesis, in many embodiments, both $R^1$ and/or both $R^3$ are the same.

Each $R^2$ independently represents H or a monovalent organic group having from 1 to 36 carbon atoms. Exemplary monovalent organic groups include $C_1$-$C_{36}$ hydrocarbyl (e.g., methyl, ethyl, propyl, isopropyl, butyl, hexyl, cyclohexyl, octyl, decyl, hexadecyl, octadecyl, eicosyl, or hexatriacontyl); $C_6$-$C_{12}$ aryl (e.g., phenyl, biphenylyl); $C_6$-$C_{12}$ alkaryl (e.g., benzyl, phenylethyl, phenyl propyl); $C_6$-$C_{12}$ aralkyl (e.g., tolyl, dimethylphenyl, trimethylphenyl); $C_5$-$C_{12}$ (meth)acryloxyalkyl; $C_5$-$C_{36}$ (meth)acryloxyalkyl; $C_1$-$C_{36}$ heterohydrocarbyl containing 6 or fewer O, N, and S atoms, combined; $C_1$-$C_{18}$ heterohydrocarbyl containing 6 or fewer O, N, and S atoms, combined; $C_1$-$C_{18}$ heterohydrocarbyl containing 6 or fewer O, N, and S atoms, combined; and $C_1$-$C_{12}$ heterohydrocarbyl containing 4 or fewer O, N, and S atoms, combined.

In some embodiments, $R^2$ comprises a polymerizable group such as, for example, a free-radically polymerizable ethylenically-unsaturated group. Multiple such groups, and their combinations, are also envisioned.

Exemplary such free-radically polymerizable ethylenically-unsaturated groups include ethenyl; allyl; methallyl; (meth)acryloyl; $C_4$-$C_{36}$ (e.g., (meth)acryloxyalkyl (e.g., (meth)acryloxyethyl, (meth)acryloxyethyl, (meth)acryloxypropyl, (meth)acryloxybutyl, (meth)acryloxyhexyl, (meth)acryloxyoctyl, (meth)acryloxydecyl, (meth)aciyloxydodecyl, (meth)acryloxyhexadecyl, (meth)acryloxyoctadecyl, (meth)aciyloxyicosyl, and (meth)acryloxytricosyl); $C_4$-$C_{36}$ (e.g., (meth)acrylamidoalkyl (e.g., (meth)acrylamidoethyl, (meth)acrylamidopropyl, (meth)acrylamidobutyl, (meth)acrylamidohexyl, (meth)acrylamidooctyl, (meth)acrylamidodecyl, (meth)aciylamidododecyl, (meth)acrylamidohexadecyl, (meth)acrylamidooctadecyl, (meth)acrylamidoicosyl, and (meth)acrylamidotricosyl); $C_6$-$C_{36}$ (meth)acryloxyalkyloxy (e.g., (meth)acryloxyethoxy, (meth)acryloxypropoxy, (meth)acryloxybutoxy, (meth)acryloxyhexoxy, (meth)acryloxyoctyloxy, (meth)acryloxydecyloxy, (meth)acryloxydodecyloxy, (meth)acryloxyhexadecyloxy, (meth)acryloxyoctadecyloxy, (meth)acryloxyicosyloxy, and (meth)acryloxytricosyloxy); and $C_6$-$C_{36}$ (meth)acrylamidoalkyloxy (e.g., (meth)acrylamidoethoxy, (meth)acrylamidopropoxy, (meth)acrylamidobutoxy, (meth)acrylamidohexoxy, (meth)acrylamidooctyloxy, (meth)acrylamidodecyloxy, (meth)acrylamidododecyloxy, (meth)acrylamidohexadecyloxy, ((meth)acrylamidooctadecyloxy, (meth)acrylamidoicosyloxy, and (meth)acrylamidotricosyloxy). In some embodiments, $R^2$ comprises a $C_5$-$C_{36}$ (meth)acryloxyheterocarbyl or a $C_5$-$C_{36}$ (meth)acrylamidoheterocarbyl group.

Spiro-compounds including polymerizable groups can be incorporated into curable compositions comprising the spiro-compound and a suitable curative for the spiro-compound, typically in an amount that is effective to cause at least partially curing of the curable composition.

The curative is typically present in the curable composition in an amount sufficient to permit an adequate rate of curing of the curable composition upon initiation of polymerization, amounts which may be readily determined by one of ordinary skill in the relevant arts.

For example, in some embodiments, a curable composition comprises a spiro-compound having a free-radically polymerizable ethylenically-unsaturated group according to the present disclosure and a free-radical initiator. Useful free-radical initiators include thermal free-radical initiators and free-radical photoinitiators. Exemplary thermal free-radical initiators include peroxides (e.g., benzoyl peroxide, chlorobenzoyl peroxide, and methyl ethyl ketone peroxide), certain azo compounds (e.g., azobisisobutyronitrile), and redox initiators (e.g., copper naphthenate).

Exemplary photoinitiators include benzoin and its derivatives such as alpha-methylbenzoin; alpha-phenylbenzoin; alpha-allylbenzoin; alpha benzylbenzoin; benzoin ethers such as benzil dimethyl ketal (e.g., available as OMNIRAD BDK from IGM Resins USA Inc., St. Charles, Illinois), benzoin methyl ether, benzoin ethyl ether, benzoin n-butyl ether; acetophenone and its derivatives such as 2-hydroxy-2-methyl-1-phenyl-1-propanone (e.g., available as OMNIRAD 1173 from IGM Resins USA Inc. and 1-hydroxycyclohexyl phenyl ketone (e.g., available as OMNIRAD 184 from IGM Resins USA Inc.); 2-methyl-1-[4-(methylthio)phenyl]-2-(4-morpholinyl)-1-propanone (e.g., available as OMNIRAD 907 from IGM Resins USA Inc.); 2-benzyl-2-(dimethylamino)-1-[4-(4-morpholinyl)phenyl]-1-butanone (e.g., available as OMNIRAD 369 from IGM Resins USA Inc.), and triaryl phosphines and phosphine oxide derivatives such as ethyl-2,4,6-trimethylbenzoylphenyl phosphinate (e.g., available as TPO-L from IGM Resins USA Inc.), and bis-(2,4,6-trimethylbenzoyl)phenylphosphine oxide (e.g., available under the trade designation OMNIRAD 819 from IGM Resins USA Inc.), pivaloin ethyl ether, anisoin ethyl ether, anthraquinones (e.g., anthraquinone, 2-ethylanthraquinone, 1-chloroanthraquinone, 1,4-dimethylanthraquinone, 1-methoxyanthraquinone, or benzanthraquinone), halomethyltriazines, benzophenone and its derivatives, iodonium salts and sulfonium salts, titanium complexes such as bis(eta5-2,4-cyclopentadien-1-yl)-bis[2,6-difluoro-3-(1H-pyrrol-1-yl) phenyl]titanium (e.g., available under the trade designation CGI 784DC from BASF, Florham Park, New Jersey); halomethylnitrobenzenes (e.g., 4-bromomethylnitrobenzene), and combinations of photoinitiators where one component is a mono- or bis-acylphosphine oxide (e.g., available under the trade designations IRGACURE 1700, IRGACURE 1800, and IRGACURE 1850 from BASF, Florham Park, New Jersey, and as OMNIRAD 4265 from IGM Resins USA Inc.).

In such embodiments, a free-radical initiator is typically present in the curable composition at a level of 0.1 to 10 percent by weight, more typically 0.5 to 5 percent by weight of the cure free-radically polymerizable components in the curable composition; however, this is not a requirement.

Curable compositions according to the present disclosure may also contain conventional additives such as one or more fillers, antioxidants, light stabilizers, fragrances, colorants, antistatic agents, flow aids, levelling agents, wetting agents, and combinations thereof.

The spiro-compound can generally be made by conventional general chemical synthetic methods that will be known to those having ordinary skill in the art.

SCHEME 1

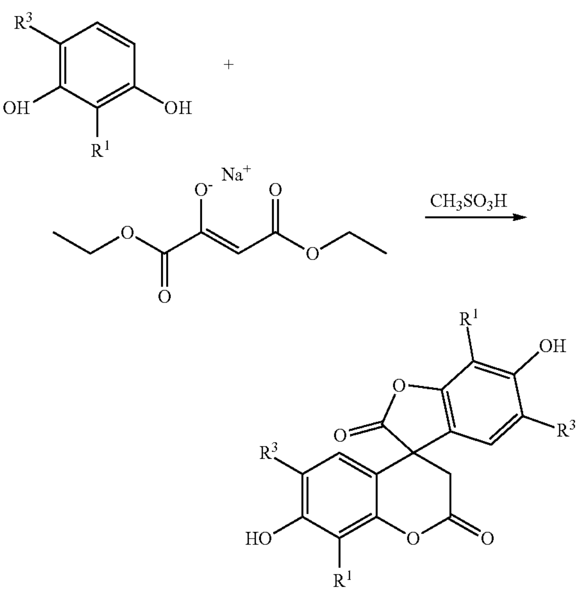

Spiro[benzofuran-3,4'-chromane]-2,2'-diones, where the Spiro carbon unites a 5-membered ring with a 6-membered ring can be conveniently prepared by condensation reactions between appropriately functionalized derivatives of benzene-1,3-diol (resorcinol) and oxalacetic acid or its esters. Resorcinol itself, or derivatives with electron-withdrawing substituents, such as 4-chlororesorcinol ($R^3$=Cl), can be reacted with the sodium salt of diethyl oxalacetate in the presence of a strong acid such as methanesulfonic acid to generate the desired product (Scheme 1).

Other catalysts for condensations of this nature are known and may be suitable for this reaction, including sulfuric acid and other strong acids, as well as Lewis acids such as $BiCl_3$, $BaCl_2$, and $AlCl_3$. Resorcinol itself, or derivatives with electron-donating groups such 2-methylresorcinol ($R^1$=Me), may also be subjected to a solid phase reaction with oxalacetic acid in the presence of phosphorus pentoxide to yield the appropriately functionalized product (Scheme 2).

SCHEME 2

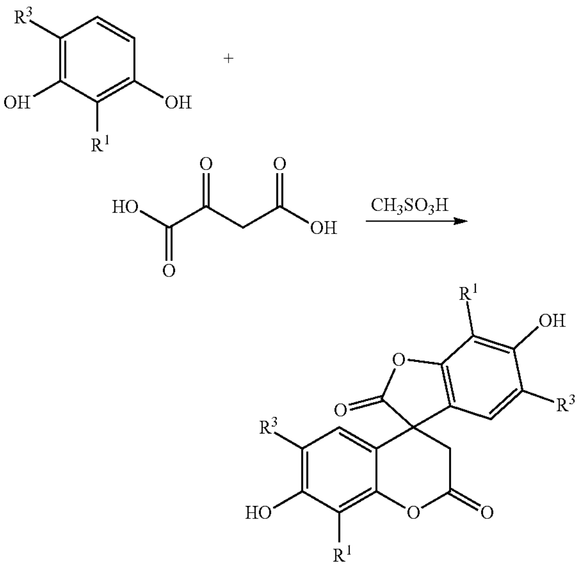

Spirobi [benzofuran]-2,2'-diones, in which the spiro carbon unites two 5-membered rings, can be prepared, for example, by condensation reactions between appropriately functionalized derivatives of benzene-1,3-diol (resorcinol) and diesters of oxomalonic acid in the presence of a strong acid such as methanesulfonic acid (Scheme 3). Other catalysts for condensations of this nature are known, including sulfuric acid and other strong Bronsted acids, as well as Lewis acids such as $BiCl_3$, $BaCl_2$, and $AlCl_3$.

SCHEME 3

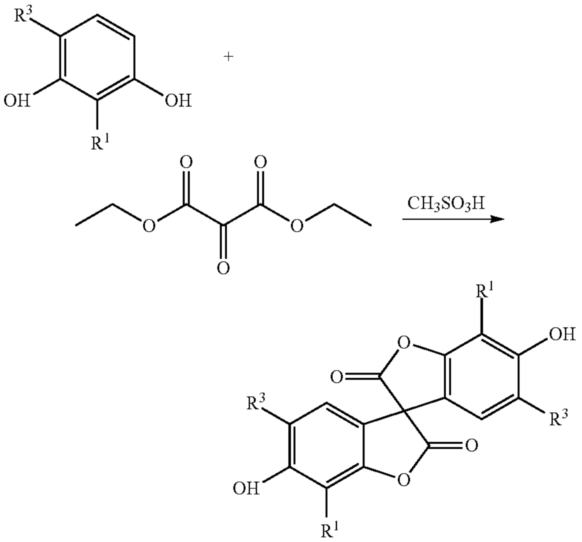

Derivatization of spirophenols (i.e., $R^2$=H) according to the present disclosure may be accomplished by various known methods. For example, reaction of acyl halides or their equivalents (e.g., esters or anhydrides) with the phenolic hydroxyl group can be used to form esters. Likewise, reaction with (meth)acryloyl chloride may result in a mono and/or di(meth)acrylate monomer. Spiro carbons in such monomers often lead to low shrinkage upon polymerization.

In another embodiment, spirophenols according to the present disclosure can be reacted with polyepoxides to form polyethers under conditions such as those described in, for example, U.S. Pat. No. 3,477,990 (Dante et al.).

Objects and advantages of this disclosure are further illustrated by the following non-limiting examples, but the particular materials and amounts thereof recited in these examples, as well as other conditions and details, should not be construed to unduly limit this disclosure.

EXAMPLES

Unless otherwise noted, all parts, percentages, ratios, etc. in the Examples and the rest of the specification are by weight.

Column chromatography purification of compounds was conducted using an ISOLARA HPFC system (an automated high-performance flash chromatography purification instrument available from Biotage, Inc, Charlottesville, Virginia). The eluent used for each purification is described in the examples.

Proton nuclear magnetic resonance ($^1H$ NMR, $^{13}C$ NMR) analyses were conducted using a BRUKER A500 NMR spectrometer (Bruker Corporation, Billerica, Massachusetts).

Resorcinol, 4-ethylresorcinol, phosphorous pentoxide, oxalacetic acid, methanesulfonic acid, ethylene carbonate, dibutyltin dilaurate (DBTDL), epichlorohydrin, and tetrabutylammonium bromide were obtained from Alfa Aesar, Ward Hill, Massachusetts.

Diethyl ketomalonate, 2-chlororesorcinol, 4-chlororesorcinol, 2-bromoresorcinol, 4-bromoresorcinol, 2-methylresorcinol, pyrogallol, and sodium diethyl oxalacetate were obtained from Oakwood Chemical, Estill, South Carolina.

Isocyanatoethyl methacrylate (IEM) was obtained from Showa Denko, Europe GmbH, Munich, Germany.

Acetone, chloroform, ethyl acetate, dichloromethane, sodium sulfate, sodium bicarbonate, and potassium chloride were obtained from EMD Millipore, Burlington, Massachusetts.

Example 1

Synthesis of 6,7'-dihydroxy-spiro[benzofuran-3,4'-chromane]-2,2'-dione

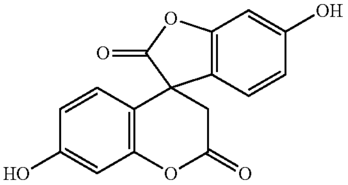 [SMILES: O=C1CC2(C(=O)Oc3cc(O)ccc32)c2ccc(O)cc2O1]

Resorcinol (10.07 g, 91.1 mmol) was ground together with oxalacetic acid (5.10 g, 38.6 mmol). The mixture was added to a 200 mL jar and phosphorus pentoxide (5.70 g, 40.2 mmol) was added in small portions with constant stirring. The mixture was heated to 70° C. for 40 minutes, then allowed to cool and stirred overnight in 100 mL deionized water. The suspension was filtered and then dried under reduced pressure to yield the desired product as a tan solid. $^{1}$H NMR (500 MHz, acetone-$d_6$) δ 9.05 (broad 2H), 7.22 (d, J=8.3 Hz, 1H), 6.80 (dd, J=8.3, 2.4 Hz, 1H), 6.76 (d, J=2.2 Hz, 1H), 6.64 (d, J=2.5 Hz, 1H), 6.59 (dd, J=8.6, 2.5 Hz, 1H), 6.55 (d, J=8.3 Hz, 1H), 3.50 (d, J=16.1 Hz, 1H), 3.15 (d, J=15.9 Hz, 1H). $^{13}$C NMR (126 MHz, acetone-$d_6$) δ 176.9, 165.0, 159.8, 159.6, 154.9, 153.5, 127.7, 125.7, 118.4, 113.7, 112.6, 112.2, 104.7, 99.1, 48.2, 37.1

Example 2

Synthesis of 5,6'-diethyl-6,7'-dihydroxy-spiro[benzofuran-3,4'-chromane]-2,2'-dione

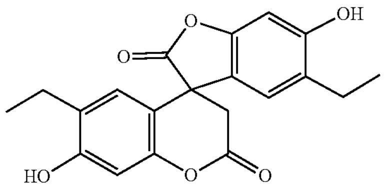 [SMILES: CCc1cc2c(cc1O)OC(=O)CC21C(=O)Oc2cc(O)c(CC)cc21]

4-Ethylresorcinol (10.12 g, 73.3 mmol) was ground together with oxalacetic acid (4.05 g=31 mmol). The mixture was added to a 200 mL jar and phosphorus pentoxide (4.4 g=31 mmol) was added in small portions with constant stirring. The mixture was heated to 90° C. for ~5 minutes, then allowed to cool and stirred overnight in 150 mL deionized water. The suspension was filtered under vacuum to yield an off-white solid. The solid was stirred sequentially five times with saturated sodium bicarbonate (150 mL) followed by water (2×150 mL), filtered, and dried under vacuum to yield the desired product as a tan solid. $^{1}$H NMR (500 MHz, acetone-$d_6$) δ 9.01 (s, 1H), 8.93 (s, 1H), 7.11 (s, 1H), 6.77 (s, 1H), 6.65 (s, 1H), 6.43 (s, 1H), 3.44 (d, J=16.1 Hz, 1H), 3.08 (d, J=15.9 Hz, 1H), 2.63 (dq, J=2.5, 7.5 Hz, 2H), 2.47 (q, J=7.6 Hz, 2H), 1.16 (t, J=7.5 Hz, 3H), 1.01 (t, J=7.5 Hz, 3H). $^{13}$C NMR (126 MHz, acetone-$d_6$) δ 177.2, 165.3, 156.9, 156.8, 152.7, 151.3, 128.2, 127.6, 126.9, 124.9, 118.1, 113.3, 104.2, 98.4, 48.5, 37.4, 23.1, 22.7, 14.1, 14.0.

Example 3

Synthesis of 5,6'-dichloro-6,7'-dihydroxy-spiro[benzofuran-3,4'-chromane]-2,2'-dione

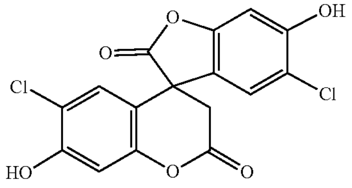 [SMILES: O=C1CC2(C(=O)Oc3cc(O)c(Cl)cc32)c2cc(Cl)c(O)cc2O1]

Sodium diethyloxalacetate (8.00 g, 38.1 mmol) was ground together with 4-chlororesorcinol (12.0 g, 83.0 mmol) and cooled in an ice bath. Methanesulfonic acid (100 mL) was added dropwise over ~45 minutes with stirring, then allowed to warm up overnight. The solution was added dropwise to 1200 mL deionized water with vigorous stirring. The suspension was stirred for a further 30 minutes, then filtered and dried under reduced pressure to yield the desired product as an off-white solid. $^{1}$H NMR (500 MHz, acetone-$d_6$) δ 9.5 (broad, 2H), 7.38 (s, 1H), 6.85 (s, 1H), 6.71 (s, 1H), 6.65 (s, 1H), 3.49 (d, J=16.1 Hz, 1H), 3.13 (d, J=16.1 Hz, 1H). $^{13}$C NMR (126 MHz, acetone-$d_6$) δ 175.9, 164.4, 155.2, 154.9, 153.6, 152.0, 127.7, 126.3, 119.0, 117.2, 116.5, 114.5, 106.0, 100.5, 39.2, 36.6.

Example 4

Synthesis of 5,6'-dibromo-6,7'-dihydroxy-spiro[benzofuran-3,4'-chromane]-2,2'-dione

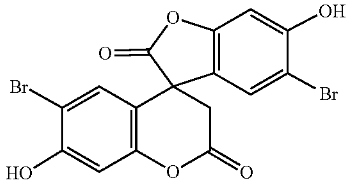 [SMILES: O=C1CC2(C(=O)Oc3cc(O)c(Br)cc32)c2cc(Br)c(O)cc2O1]

Sodium diethyl oxalacetate (2.01 g=9.57 mmol) was mixed with 4-bromoresorcinol (4.06 g=21.5 mmol), stirred and cooled in an ice bath. Methanesulfonic acid (20 mL) was added dropwise over ~20 minutes, and the mixture stirred and allowed to warm up overnight. The following morning, the solution was added dropwise to 600 mL deionized water with vigorous stirring. After 15 minutes, the mixture was filtered and dried to yield the desired product as a tan solid. $^{1}$H NMR (500 MHz, acetone-$d_6$) δ 9.67 (broad, 2H), 7.65 (s, 1H), 6.98 (s, 1H), 6.91 (1H), 6.83 (s, 1H), 3.63 (d, J=16.1 Hz, 1H), 3.26 (d, J=16.1 Hz, 1H). $^{13}$C NMR (126 MHz, acetone-$d_6$) δ 175.9, 164.3, 156.2, 156.0, 154.3, 152.7, 130.6, 129.2, 119.6, 115.1, 105.7, 105.6, 105.0, 100.2, 48.3, 36.6.

Example 5

Synthesis of 7,8'-dibromo-6,7'-dihydroxy-spiro[benzofuran-3,4'-chromane]-2,2'-dione

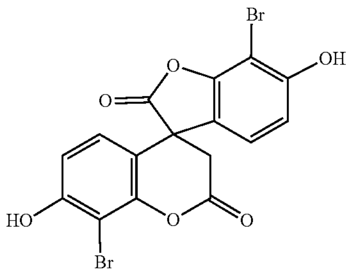 [SMILES: O=C1CC2(C(=O)Oc3c2ccc(O)c3Br)c2ccc(O)c(Br)c2O1]

Sodium diethyl oxalacetate (5.40 g, 28.5 mmol) was mixed with 2-bromoresorcinol (10.53 g, 55.72 mmol), stirred and cooled in an ice bath. Methanesulfonic acid (60 mL) was added dropwise over 60 minutes, and the mixture stirred and allowed to warm up overnight. The following morning, the solution was added dropwise to 800 mL deionized water with vigorous stirring. After 30 minutes, the mixture was filtered and dried under reduced pressure to yield the desired product as a brown solid. $^1H$ NMR (500 MHz, acetone-$d_6$) δ 9.67 (s, 1H), 9.67 (s, 1H), 7.25 (d, J=8.3 Hz, 1H), 6.96 (d, J=8.1 Hz, 1H), 6.77 (d, J=8.6 Hz, 1H), 6.64 (d, J=8.6 Hz, 1H), 3.63 (d, J=15.9 Hz, 1H), 3.39 (d, J=15.9 Hz, 1H). $^{13}C$ NMR (126 MHz, acetone-$d_6$) δ 175.5, 164.1, 156.5, 156.5, 153.1, 150.6, 126.3, 124.3, 119.2, 114.7, 112.7, 111.9, 99.6, 92.6, 39.2, 36.6.

Example 6

Synthesis of 6,7'-dihydroxy-7,8'-dimethyl-spiro[benzofuran-3,4'-chromane]-2,2'-dione

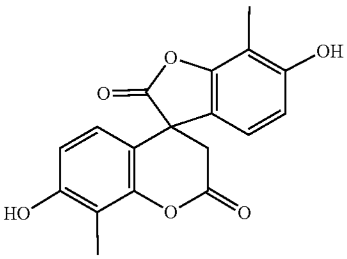 [SMILES: Cc1c(O)ccc2c1OC(=O)CC21C(=O)Oc2c1ccc(O)c2C]

2-Methylresorcinol (1.12 g, 8.2 mmol) was stirred together with oxalacetic acid (0.59 g, 3.8 mmol) in a 40 mL vial and phosphorus pentoxide (0.61 g, 4.3 mmol) was added in small portions with constant stirring. The mixture was heated to 80° C. for ~5 minutes, then allowed to cool and stirred overnight in 150 mL deionized water. The following morning the suspension was filtered under vacuum to yield a red solid. The solid was stirred sequentially three times with saturated sodium bicarbonate (30 mL) followed by water (30 mL) and filtered. The solid was dissolved in acetone, filtered, and then solvent removed under vacuum, yielding a brown solid. $^1H$ NMR (500 MHz, acetone-$d_6$) δ 8.87 (broad, 2H), 7.00 (d, J=8.3 Hz, 1H), 6.79 (d, J=2.0 Hz, 1H), 6.59 (d, J=8.6 Hz, 1H), 6.36 (d, J=8.6 Hz, 1H), 3.42 (d, J=15.9 Hz, 1H), 3.12 (d, J=15.9 Hz, 1H), 2.19 (s, 3H), 2.18 (s, 3H). $^{13}C$ NMR (126 MHz, acetone-$d_6$) d 177.0, 165.1, 157.5, 157.2, 153.3, 151.5, 124.1, 122.3, 118.5, 114.0, 113.6, 111.6, 111.0, 108.7, 49.1, 37.1, 8.4, 8.2.

Example 7

Synthesis of 6,7,7',8'-tetrahydroxyspiro[benzofuran-3,4'-chromane]-2,2'-dione

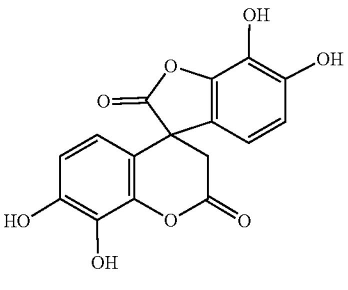 [SMILES: O=C1CC2(C(=O)Oc3c2ccc(O)c3O)c2ccc(O)c(O)c2O1]

Pyrogallol (1.008 g, 7.99 mmol) was stirred with oxalacetic acid (0.4956 g, 3.75 mmol) in a 40 mL vial. Phosphorus pentoxide (0.607 g=4.17 mmol) was added with stirring and the reaction initiated with a hot air gun. The reaction mixture was heated at 70° C. for five minutes, then allowed to cool.

The product was extracted into 50 mL ethyl acetate and 10 ml water to remove acid. The organic phase was separated off, then extracted with 10 mL brine, dried over sodium sulfate and filtered. The solvent was then removed under reduced pressure to yield the desired product as a brown solid. $^1H$ NMR (500 MHz, acetone-$d_6$) δ 6.79 (d, J=8.3 Hz, 1H), 6.71 (d, J=8.1 Hz, 1H), 6.58 (d, J=8.3 Hz, 8 1H), 6.07 (d, J=8.6 Hz, 1H), 3.47 (d, J=16.1 Hz, 1H), 3.15 (d, J=16.1 Hz, 1H).

Example 8

Synthesis of 5,5'-dichloro-6,6'-dihydroxy-3,3'-spirobi[benzofuran]-2,2'-dione

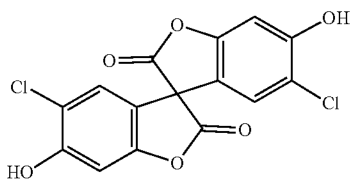 [SMILES: O=C1Oc2cc(O)c(Cl)cc2C12C(=O)Oc1cc(O)c(Cl)cc12]

Diethyl ketomalonate (4.0 mL, 26.2 mmol) was mixed with 4-chlororesorcinol (7.60 g, 52.6 mmol) forming a brown slurry. Methanesulfonic acid (60 mL) was added dropwise and the suspension heated to 50° C. and stirred overnight. The reaction mixture was then added dropwise to 600 mL deionized water with vigorous stirring and then stirred for a further 30 minutes. It was then filtered, washed on the filter with deionized water (5×50 mL) and dried on the filter to yield the desired product as an off-white solid. $^1H$ NMR (500 MHz, acetone-$d_6$) δ 9.74 (broad, 2H), 7.52 (s, 2H), 7.04 (s, 2H).

Example 9

Synthesis of 5,5'-dibromo-6,6'-dihydroxy-3,3'-spirobi[benzofuran]-2,2'-dione

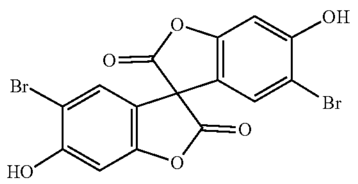 [SMILES: O=C1Oc2cc(O)c(Br)cc2C12C(=O)Oc1cc(O)c(Br)cc12]

Diethyl ketomalonate (1.0 mL, 6.56 mmol) was mixed with 4-bromoresorcinol (2.64 g, 14.0 mmol) and cooled in an ice bath. Methanesulfonic acid (20 mL) was added dropwise over 15 minutes and the reaction mixture left to warm up overnight. The reaction mixture was then added dropwise to 300 mL deionized water with vigorous stirring and then stirred for a further 30 minutes. It was then filtered, washed on the filter with deionized water (5×50 mL) and dried under reduced pressure to yield the desired product as a tan solid. $^1H$ NMR (500 MHz, acetone-$d_6$) δ 9.86 (broad, 2H), 7.66 (s, 2H), 7.02 (s, 2H). $^{13}C$ NMR (126 MHz, acetone-$d_6$) δ 170.3, 156.9, 155.2, 129.6, 117.4, 105.9, 100.2, 58.7.

Example 10

Synthesis of 5,6'-diethyl-6,7'-bis(2-hydroxyethoxy) spiro[benzofuran-3,4'-chromane]-2,2'-dione

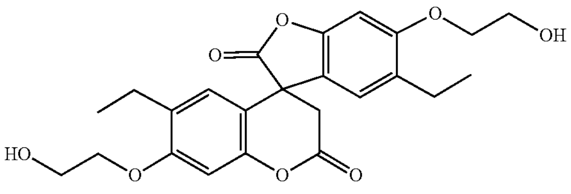 [SMILES: CCc1cc2c(cc1OCCO)OC(=O)CC21C(=O)Oc2cc(OCCO)c(CC)cc21]

Ethylene carbonate (1.042 g, 11.83 mmol) was melted with a hot air gun and added by pipet to 5,6'-diethyl-6,7'-dihydroxy-3,3'-spiro[benzofuran-3,4'-chromane]-2,2'-dione (1.737 g, 4.90 mmol) in a 20 mL vial, and heated to 155° C. Potassium chloride (40.5 mg, 0.54 mmol) was added and the vial heated with stirring for 6.5 hours. The solid product was triturated in deionized water overnight, then filtered and dried under reduced pressure to yield the desired product as a brown solid. $^{1}H$ NMR (500 MHz, acetone-$d_6$) δ 7.17 (s, 1H), 6.99 (s, 1H), 6.80 (s, 1H), 6.46 (s, 1H), 4.19 (m, 2H), 4.15 (t, J=4.8 Hz, 2H), 4.07 (m, 2H), 3.96 (m, 2H), 3.92 (m, 2H), 3.50 (d, J=16.1 Hz, 1H), 3.14 (d, J=15.9 Hz, 1H), 2.67 (q, J=7.5 Hz, 2H), 2.49 (q, J=7.5 Hz, 2H), 1.15 (t, J=7.6 Hz, 3H), 1.00 (t, J=7.5 Hz, 3H).

Example 11

Synthesis of 7,8'-dimethyl-6,7'-bis(2-hydroxy-ethoxy)spiro[benzofuran-3,4'-chromane]-2,2'-dione

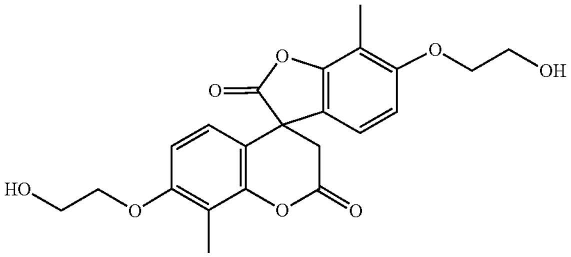 [SMILES: Cc1c(OCCO)ccc2c1OC(=O)CC21C(=O)Oc2c1ccc(OCCO)c2C]

Ethylene carbonate (1.199 g, 13.62 mmol) was melted with a hot air gun and added by pipet to 7,8'-dimethyl-6,7'-dihydroxy-3,3'-spiro[benzofuran-3,4'-chromane]-2,2'-dione (1.995 g, 6.11 mmol) in a 20 mL vial, and heated to 155° C. with stirring. Potassium chloride (44.2 mg, 0.60 mmol) was added and the vial heated for 18 hours. The solid product was triturated in deionized water, filtered and dried under reduced pressure to yield the desired product as a tan solid. $^{1}H$ NMR (500 MHz, acetone-$d_6$) δ 7.16 (d, J=8.3 Hz, 1H), 6.91 (d, J=8.3 Hz, 1H), 6.72 (d, J=8.8 Hz, 1H), 6.50 (d, J=8.6 Hz, 1H), 4.16 (t, J=4.8 Hz, 2H), 4.08 (t, J=4.8 Hz, 2H), 3.93 (m, 2H), 3.88 (m, 2H), 3.56 (s, 2H), 3.48 (d, J=16.1 Hz, 1H), 3.17 (d, J=15.9 Hz, 1H), 2.21 (s, 3H), 2.20 (s, 3H).

Example 12

Synthesis of (5,6'-diethyl-2,2'-dioxo-6-prop-2-enoyloxy-spiro[benzofuran-3,4'-chromane]-7'-yl) prop-2-enoate

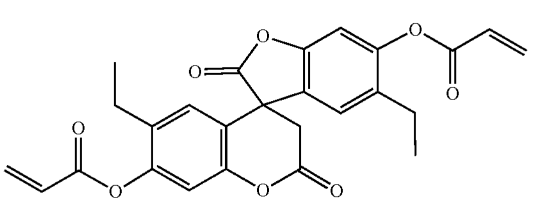 [SMILES: C=CC(=O)Oc1cc2c(cc1CC)C1(CC(=O)O2)C(=O)Oc2cc(OC(=O)C=C)c(CC)cc21]

Dry triethylamine (2.5 mL, 18.0 mmol) was added to a solution of 5,6'-diethyl-6,7'-dihydroxy-3,3'-spiro[benzofuran-3,4'-chromane]-2,2'-dione (1.251 g, 3.53 mmol) in dry tetrahydrofuran (10 mL). The solution was cooled in a dry ice bath and acryloyl chloride (1.5 mL, 19.6 mmol) was added in five portions over two hours. The reaction mixture was allowed to warm up with stirring overnight, then extracted with ethyl acetate (100 mL) and deionized water (100 mL). The organic phase was further extracted with brine (100 mL), dried over anhydrous sodium sulfate, and filtered. Solvent was removed under reduced pressure to yield the desired product as a yellow solid. $^{1}H$ NMR (500 MHz, acetone-$d_6$) δ 7.49 (s, 1H), 7.22 (s, 1H), 7.09 (s, 1H), 6.74 (s, 1H), 6.63 (m, 2H), 6.46 (m, 2H), 6.18 (m, 2H), 3.71 (d, J=16.1 Hz, 1H), 3.40 (d, J=16.1 Hz, 1H), 2.59 (q, J=7.6 Hz, 2H), 2.43 (q, J=7.6 Hz, 2H), 1.15 (t, J=7.6 Hz, 3H), 0.99 (t, J=7.5 Hz, 3H).

Example 13

Synthesis of (5,6'-dichloro-2,2'-dioxo-6-prop-2-enoyloxy-spiro[benzofuran-3,4'-chromane]-7'-yl) prop-2-enoate

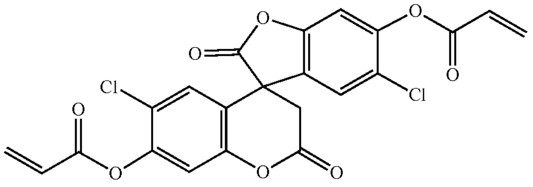 [SMILES: C=CC(=O)Oc1cc2c(cc1Cl)C1(CC(=O)O2)C(=O)Oc2cc(OC(=O)C=C)c(Cl)cc21]

Dry triethylamine (2.5 mL, 18.0 mmol) was added to a solution of 5,6'-dichloro-6,7'-dihydroxy-3,3'-spiro[benzofuran-3,4'-chromane]-2,2'-dione (1.223 g, 3.33 mmol) in dry tetrahydrofuran (20 mL). The mixture was cooled in a dry ice bath and acryloyl chloride (1.5 mL, 19.6 mmol) was added in five portions over two hours. The reaction mixture was allowed to warm up with stirring overnight, then extracted with ethyl acetate (50 mL) and deionized water (150 mL). The organic phase was further extracted with brine (100 mL), dried over anhydrous sodium sulfate, and filtered. Solvent was removed under reduced pressure, and the resulting solid further extracted with diethyl ether, filtered and dried under reduced pressure to yield the desired product as a yellow solid. $^{1}H$ NMR (500 MHz, acetone-$d_6$) δ 7.85 (s, 1H), 7.48 (s, 1H), 7.34 (s, 1H), 7.10 (s, 1H), 6.66

(m, 2H), 6.45 (m, 2H), 6.23 (m, 2H), 3.85 (d, J=16.1 Hz, 1H), 3.55 (d, J=16.1 Hz, 1H).

Example 14

Synthesis of 2-[2-[5,6'-diethyl-6-[2-[2-(2-methylprop-2-enoyloxy)ethylcarbamoyloxy]ethoxy]-2,2'-dioxo-spiro[benzofuran-3,4'-chromane]-7'-yl]oxy-ethoxycarbonylamino]ethyl 2-methylprop-2-enoate

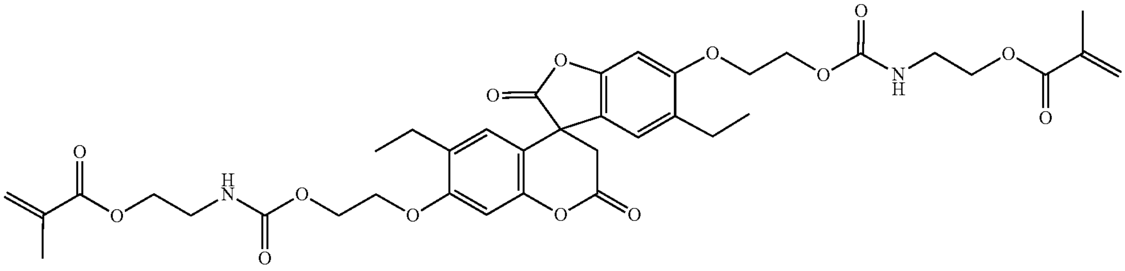 [SMILES: C=C(C)C(=O)OCCNC(=O)OCCOc1cc2c(cc1CC)C1(CC(=O)O2)C(=O)Oc2cc(OCCOC(=O)NCCOC(=O)C(=C)C)c(CC)cc21]

5,6'-Diethyl-6,7'-bis(2-hydroxyethoxy)spiro[benzofuran-3,4'-chromane]-2,2'-dione (1.006 g, 2.15 mmol) was dissolved in dry tetrahydrofuran. IEM (0.65 mL, 4.6 mmol) and DBTDL (0.012 mL, 0.02 mmol) were added and the reaction mixture heated to 60° C. for 1 hour. It was then allowed to cool with stirring overnight. The solution was precipitated into hexanes (100 mL), and the solvent decanted. Residual solvent was removed under reduced pressure. The product was chromatographed over silica (4.8%-20% acetone in chloroform) to yield the desired product as a yellow foam. $^1$H NMR (500 MHz, acetone-$d_6$) δ 7.18 (s, 1H), 7.00 (s, 1H), 6.81 (s, 1H), 6.62 (br, 2H), 6.47 (s, 1H), 6.09 (s, 1H), 6.07 (s, 1H), 5.60 (m, 1H), 5.59 (m, 1H), 4.46 (m, 2H), 4.41 (m, 2H), 4.31 (m, 2H), 4.27 (m, 2H), 4.19 (m, 4H), 3.50 (d, J=15.9 Hz, 1H), 3.45 (m, 4H), 3.14 (d, J=16.1 Hz, 1H), 2.63 (q, J=7.5 Hz, 2H), 2.45 (q, J=7.5 Hz, 2H), 1.89 (s, 3H), 1.88 (s, 3H), 1.14 (t, J=7.4 Hz, 3H), 0.99 (t, J=7.4 Hz, 3H).

Example 15

Synthesis of 2-[2-[7,8'-dimethyl-6-[2-[2-(2-methylprop-2-enoyloxy)ethylcarbamoyloxy]ethoxy]-2,2'-dioxo-spiro[benzofuran-3,4'-chromane]-7'-yl]oxy-ethoxycarbonylamino]ethyl 2-methylprop-2-enoate

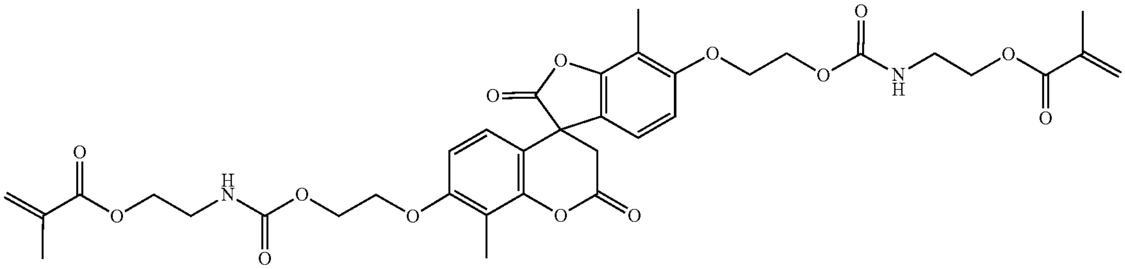 [SMILES: C=C(C)C(=O)OCCNC(=O)OCCOc1ccc2c(c1C)OC(=O)CC21C(=O)Oc2c1ccc(OCCOC(=O)NCCOC(=O)C(=C)C)c2C]

7,8'-Dimethyl-6,7'-bis(2-hydroxyethoxy)spiro[benzofuran-3,4'-chromane]-2,2'-dione (1.003 g, 2.42 mmol) was dissolved in dry tetrahydrofuran. IEM (0.65 mL, 4.6 mmol) and DBTDL (0.012 mL, 0.02 mmol) were added and the reaction mixture heated to 60° C. for 1 hour. It was then allowed to cool with stirring overnight. The solution was precipitated into hexanes (100 mL), and the solvent decanted. Residual solvent was removed under reduced pressure. The product was chromatographed over silica (4.8%-20% acetone in chloroform) to yield the desired product as a pale orange foam. $^1$H NMR (500 MHz, acetone-$d_6$) δ 7.17 (d, J=8.3 Hz, 1H), 6.92 (d, J=8.6 Hz, 1H), 6.72 (d, J=8.6 Hz, 1H), 6.63 (br, 2H), 6.50 (d, J=8.6 Hz, 1H), 6.09 (s, 1H), 6.07 (s, 1H), 5.61 (m, 1H), 5.59 (m, 1H), 4.43 (m, 2H), 4.38 (m, 2H), 4.20 (m, 6H), 4.08 (t, J=4.8 Hz, 2H), 3.93 (m, 2H), 3.88 (m, 2H), 3.49 (d, J=16.1 Hz, 1H), 3.45 (m, 4H) 3.18 (d, J=15.9 Hz, 1H), 2.18 (s, 3H), 2.17 (s, 3H), 1.89 (s, 3H), 1.88 (s, 3H).

The preceding description, given in order to enable one of ordinary skill in the art to practice the claimed disclosure, is not to be construed as limiting the scope of the disclosure, which is defined by the claims and all equivalents thereto.

What is claimed is:

1. A spiro-compound represented by the formula

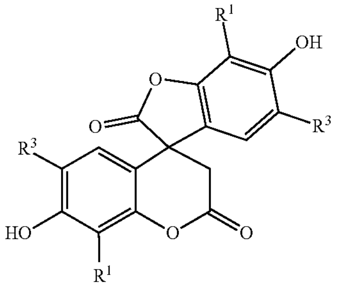

wherein:

each $R^1$ independently represents H, $C_1$-$C_6$ alkyl, hydroxyl, or a halogen; and each $R^3$ independently represents H, $C_1$-$C_6$ alkyl, or halogen.

2. The spiro-compound of claim 1, wherein the spiro-compound is represented by the formula:

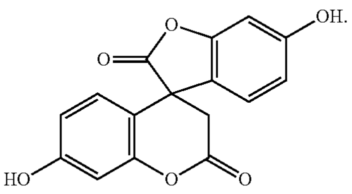 [SMILES: O=C1CC2(C(=O)Oc3cc(O)ccc32)c2ccc(O)cc2O1]

3. The spiro-compound of claim 1, wherein the spiro-compound is represented by the formula:

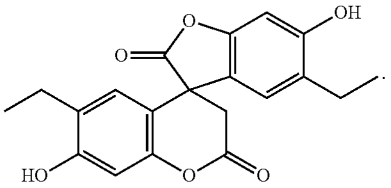 [SMILES: CCc1cc2c(cc1O)OC(=O)CC21C(=O)Oc2cc(O)c(CC)cc21]

4. The spiro-compound of claim 1, wherein the spiro-compound is represented by the formula:

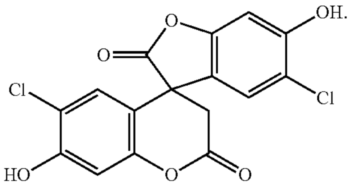 [SMILES: O=C1CC2(C(=O)Oc3cc(O)c(Cl)cc32)c2cc(Cl)c(O)cc2O1]

5. The spiro-compound of claim 1, wherein the spiro-compound is represented by the formula:

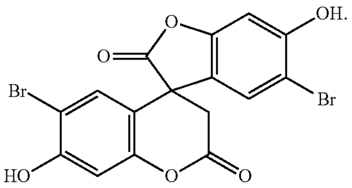 [SMILES: O=C1CC2(C(=O)Oc3cc(O)c(Br)cc32)c2cc(Br)c(O)cc2O1]

6. The spiro-compound of claim 1, wherein the spiro-compound is represented by the formula:

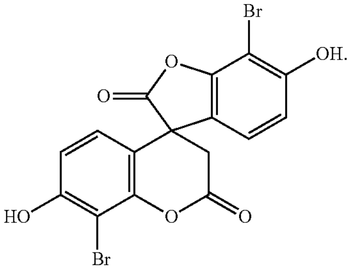 [SMILES: O=C1CC2(C(=O)Oc3c2ccc(O)c3Br)c2ccc(O)c(Br)c2O1]

7. The spiro-compound of claim 1, wherein the spiro-compound is represented by the formula:

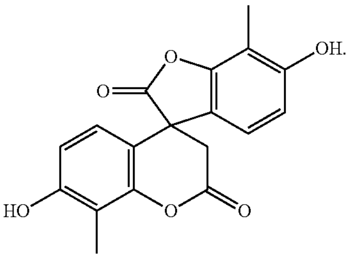 [SMILES: Cc1c(O)ccc2c1OC(=O)CC21C(=O)Oc2c1ccc(O)c2C]

8. The spiro-compound of claim 1, wherein the spiro-compound is represented by the formula:

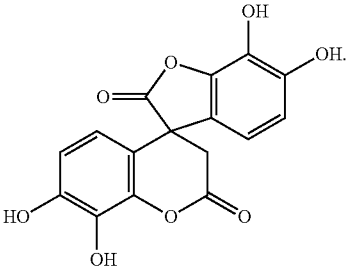 [SMILES: O=C1CC2(C(=O)Oc3c2ccc(O)c3O)c2ccc(O)c(O)c2O1]

9. A spiro-compound represented by the formula

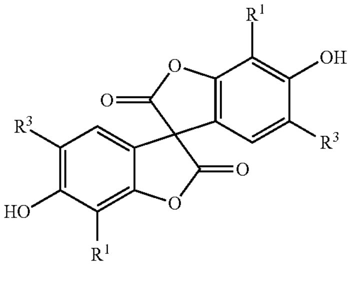

wherein:

each $R^1$ independently represents H, $C_1$-$C_6$ alkyl, hydroxyl, or a halogen; and each $R^3$ independently represents H, $C_1$-$C_6$ alkyl, or halogen.

10. The spiro-compound of claim 9, wherein the spiro-compound is represented by the formula:
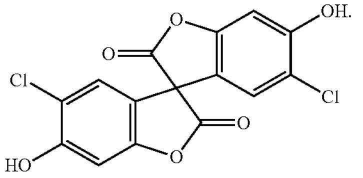 [SMILES: O=C1Oc2cc(O)c(Cl)cc2C12C(=O)Oc1cc(O)c(Cl)cc12]
11. The spiro-compound of claim 9, wherein the spiro-compound is represented by the formula:
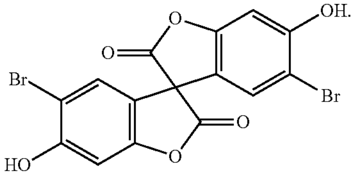 [SMILES: O=C1Oc2cc(O)c(Br)cc2C12C(=O)Oc1cc(O)c(Br)cc12]
12. A spiro-compound selected from the group consisting of compounds represented by the following formulas:
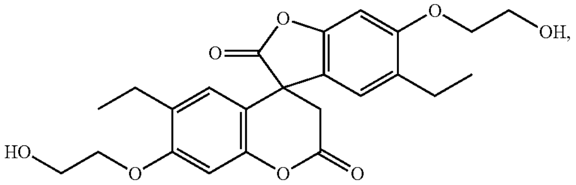
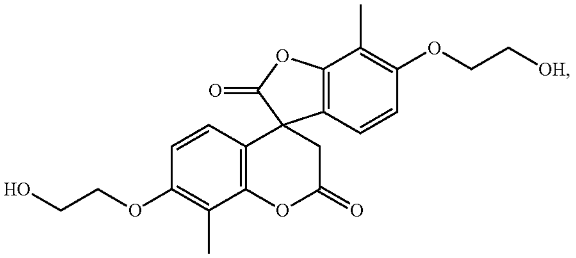
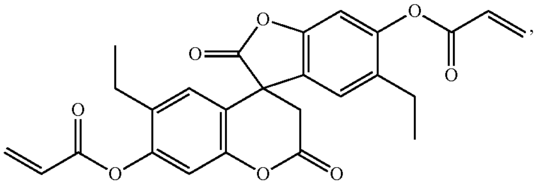
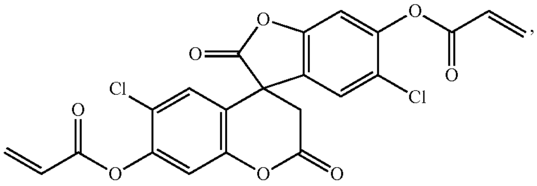
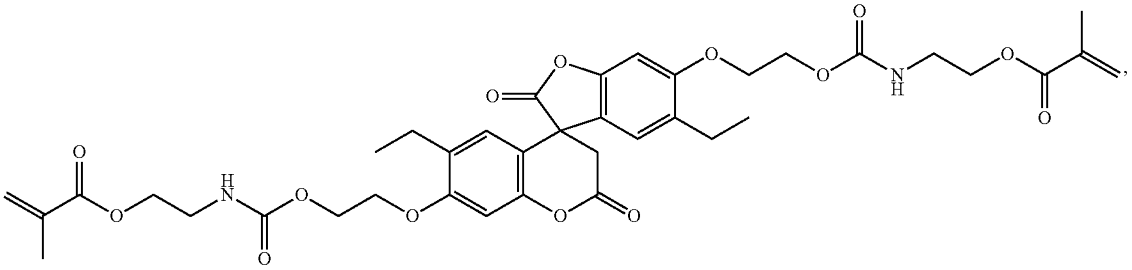
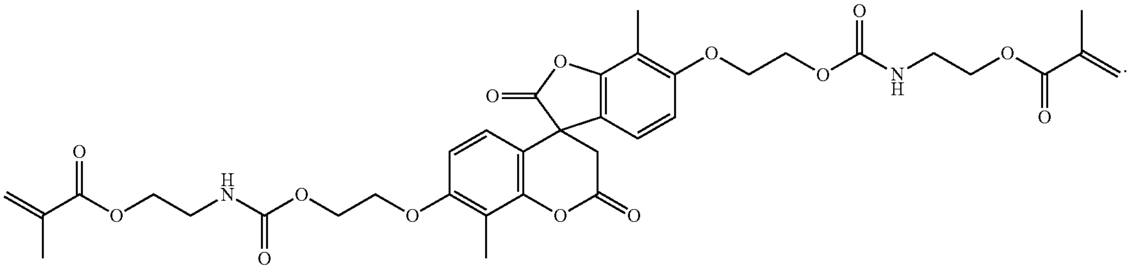
* * * * *